US00PP31875P2

(12) United States Plant Patent
Negley et al.

(10) Patent No.: US PP31,875 P2
(45) Date of Patent: Jun. 16, 2020

(54) RHUBARB PLANT NAMED 'GARRUSARSABZAR'

(50) Latin Name: ***Rheum rhabarbarum* L.**
Varietal Denomination: GARrusarsabzar

(71) Applicant: Early Morning LLC, Greendale, IN (US)

(72) Inventors: Sarah J. Negley, Mechanicsburg, OH (US); Sabrina A. Detrick, Houston, OH (US); Keith W. Zary, Missoula, MT (US)

(73) Assignee: Early Morning, LLC, Greendale, IN (US)

( * ) Notice: Subject to any disclaimer, the term of this patent is extended or adjusted under 35 U.S.C. 154(b) by 0 days.

(21) Appl. No.: 16/602,072

(22) Filed: Jul. 30, 2019

(51) Int. Cl.
*A01H 5/04* (2018.01)
*A01H 6/00* (2018.01)

(52) U.S. Cl.
USPC ..... Plt./262
CPC ..... *A01H 6/00* (2018.05)

(58) Field of Classification Search
USPC ..... Plt./262, 258
CPC ..... A01H 5/04
See application file for complete search history.

*Primary Examiner* — Kent L Bell
(74) *Attorney, Agent, or Firm* — Barbara Campbell; Cochran Freund & Young LLC

(57) ABSTRACT

A new and distinct variety of rhubarb plant having heat tolerance, a red petiole color, and excellent cooked flavor and color, is disclosed.

2 Drawing Sheets

Genus and species: *Rheum rhabarbarum* L.
Denomination: 'GARrusarsabzar'.

BACKGROUND

'GARrusarsabzar' is a new and distinct variety of rhubarb plant. 'GARrusarsabzar' originated from a single plant selection derived from a seed lot of rhubarb plants collected from an open-pollinated crop of the variety 'Victoria' (unpatented) in Melbourne, Australia in 2012.

The resulting seeds from the open-pollination were collected and planted in 2013 in Melbourne, Australia and grown for three years. In 2016, a single plant was selected and named 'GARrusarsabzar'. Selection criteria included heat tolerance, red petiole color, and excellent cooked flavor and color.

'GARrusarsabzar' was first asexually propagated in 2016 in Melbourne, Australia by division of the crown of the plant. 'GARrusarsabzar' was subsequently propagated via tissue culture in 2017 and 2018 in Tipp City, Ohio.

Other subsequent asexual propagations were conducted in controlled environments in Melbourne, Australia and Tipp City, Ohio and demonstrate that 'GARrusarsabzar' reproduces true to type in successive generations of asexual reproduction via division of the crown of the plant and tissue culture.

SUMMARY

The following are the most outstanding and distinguishing characteristics of this new variety when grown under normal horticultural practices in Tipp City, Ohio.

1. A rhubarb plant having heat tolerance, a red petiole color; and
2. Excellent cooked flavor and color.

DESCRIPTION OF THE PHOTOGRAPHS

This new rhubarb plant is illustrated by the accompanying photographs which show the plant's overall plant habit including form, foliage, and flowers. The photographs are of a 3-year old plant grown outdoors in Tipp City, Ohio in May 2019. The colors shown are as true as can be reasonably obtained by conventional photographic procedures.

DETAILED DESCRIPTION

Figure 1:
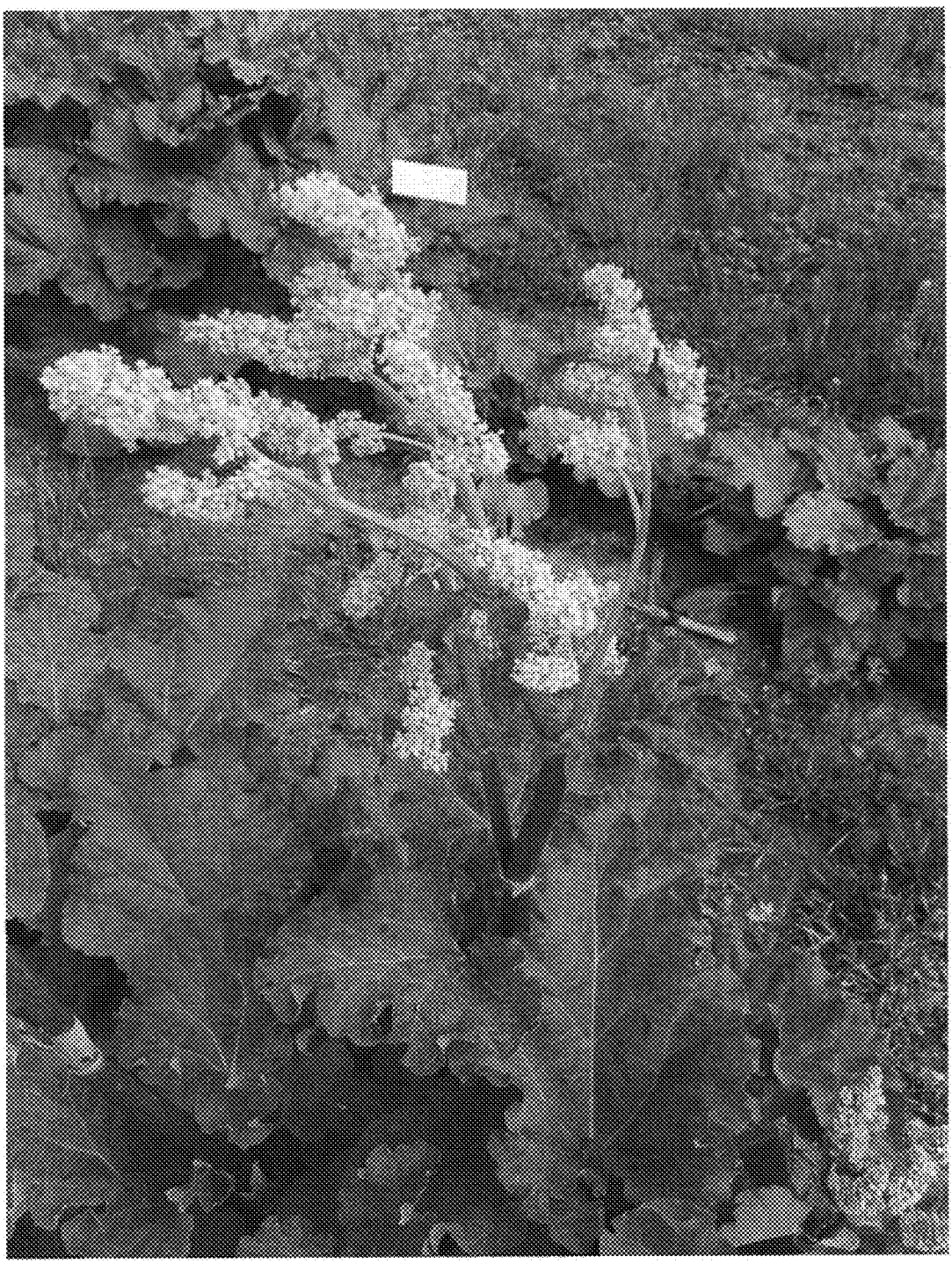
FIG. 1 shows the overall plant habit of 'GARrusarsabzar'.
Figure 2:
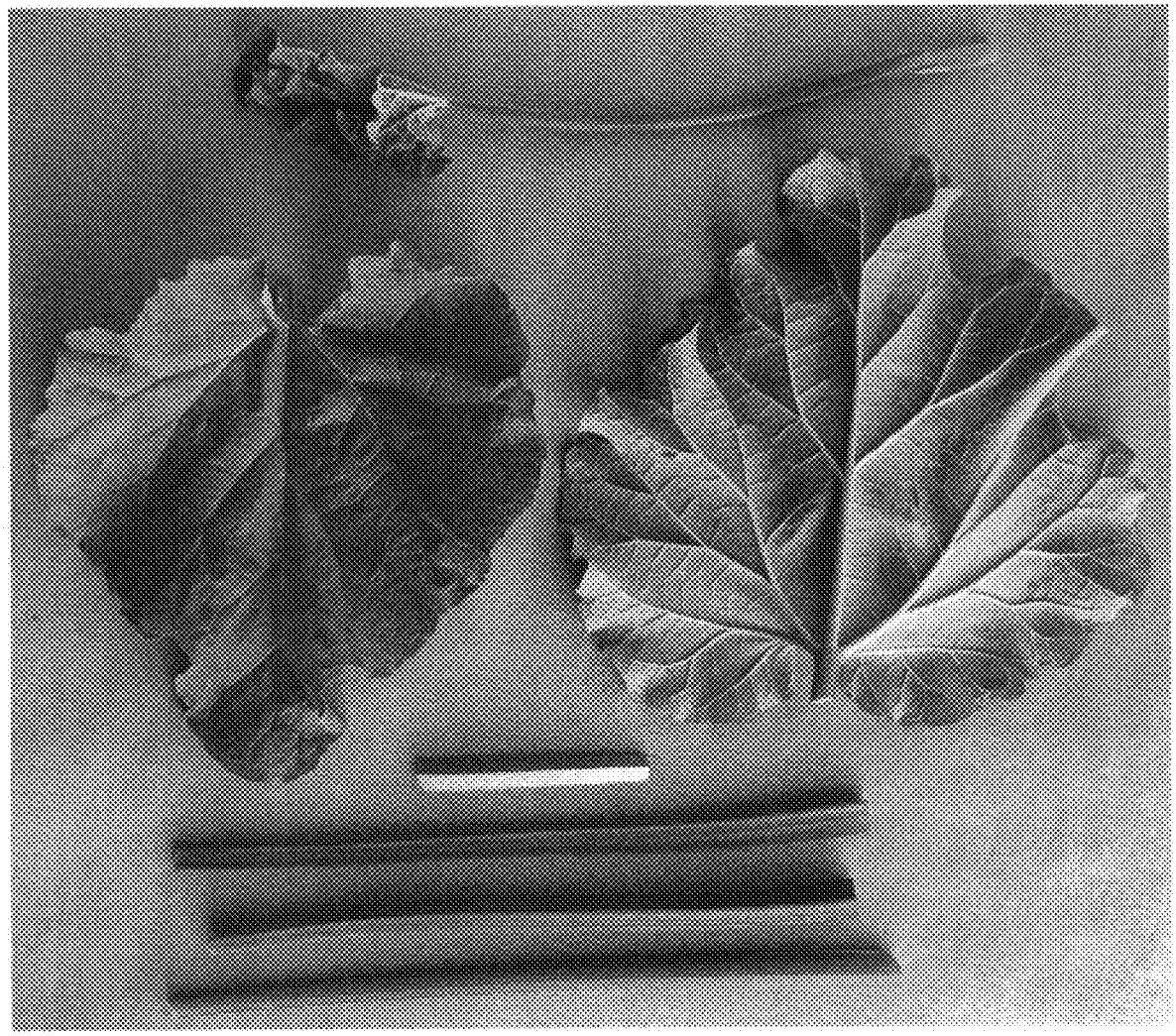
FIG. 2 shows the following from top to bottom and left to right: an individual petiole stalk with a leaf; the upper surface of an individual leaf; the lower surface of an individual leaf; a cross section of a segment of a petiole; and the last three rows show three individual petiole stalks.

The following detailed descriptions set forth the distinctive characteristics of 'GARrusarsabzar'. The data which define these characteristics were collected outdoors in Tipp City, Ohio in May 2019 from a 3-year-old plant. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:
- *Family.*—Polygonaceae.
- *Species.*—*Rheum rhabarbarum* L.
- *Common name.*—Rhubarb.
- *Variety.*—'GARrusarsabzar'.

Parentage: Open-pollination of seedlings of 'Victoria' (unpatented).

Plant:
- *Type.*—Herbaceous rhizomatous perennial.
- *Hardiness.*—Zone 3 to 8.
- *Time of emergence.*—Early spring as soon as the frost has left the ground.
- *Plant height.*—50.0 cm to 60.0 cm.
- *Plant width.*—80.0 cm to 90.0 cm.

*Habit.*—Clumping with 4 crowns at three years of age in Tipp City, Ohio.

*Propagation type.*—By division of the crown of the plant and by tissue culture.

*Time to initiate roots.*—Roots initiate from the division after planting as soon as the soil temperature is above freezing. In tissue culture, roots emerge from the propagule with two weeks of applying rooting hormones.

*Root description.*—Rhizome, thick fleshy roots, RHS N200B.

Leaf:

*Arrangement.*—Simple.

*Shape.*—Rosette.

*Venation type.*—Pinnate.

*Venation color.*—Upper surface: RHS N170D near the base and changing to RHS 157C to RHS 157D near the apex. Lower surface: RHS N170D near the base and changing to RHS 157A on the Mid-rib above the base and RHS 157A on the laterals.

*Apex.*—Obtuse to cordate.

*Base.*—Lobes overlap.

*Margin.*—Undulating.

*Length.*—28.0 cm to 30.0 cm.

*Width.*—26.0 cm to 28.0 cm.

*Surface texture.*—Upper surface: Glabrous. Lower surface: Pubescent on the veins.

*Leaf color.*—Immature leaf: Upper surface: RHS 137A. Lower surface: RHS 146A. Mature leaf: Upper surface: RHS 137B. Lower surface: RHS 148B.

*Petiole.*—Length: 35.0 cm to 40 cm, 1.5 cm wide and D-shaped in cross section. Diameter: 1.5 cm. Thickness near base: 1.7 cm. Color: RHS 53A on the exterior and interior flesh is RHS 157A. Texture: Smooth.

Inflorescence:

*Type.*—Large panicle.

*Width.*—22.0 cm to 26.0 cm.

*Length.*—40.0 cm to 45.0 cm.

*Height.*—70.0 cm to 75.0 cm.

*Number of flowers per inflorescence.*—In the entire panicle (whole inflorescence), there are over 3,000 flowers.

*Pedicel.*—Length: 0.4 cm. Diameter: 0.1 cm. Color: RHS 145C. Texture: Glabrous.

*Peduncle.*—Length: 50 cm. Diameter: 4.0 cm. Color: RHS 137B. Texture: Glabrous, hollow, branched (1-3 branches).

*Bloom period.*—May and June in Tipp City, Ohio.

Bud:

*Shape.*—Ovoid.

*Height.*—0.3 cm.

*Width.*—0.25 cm.

*Color.*—RHS 155B.

*Texture.*—Smooth.

Perianth:

*Shape.*—Obovate.

*Length.*—0.3 cm.

*Width.*—0.3 cm.

*Quantity of flowers and buds at a time per plant.*—Over 3,000 per flowering stem.

*Flowering season.*—May to June.

*Lastingness of individual flowers on the plant.*—3 to 4 days, but entire inflorescence is up to 2 weeks.

*Fragrance.*—There is an unpleasant scent.

*Arrangement.*—Six tepals per flower.

*Tepals.*—Length: 0.1 cm. Width: 0.1 cm. Shape: Obovate. Apex: Obtuse. Base: Fused. Margin: Entire. Texture (both upper and lower surfaces): Glabrous. Color (both upper and lower surfaces): RHS 157B.

Reproductive organs:

*Stamens.*—Quantity per flower: 9. Filament: Length: 0.2 cm. Color: RHS 158D. Anther: Length: 0.5 cm. Pollen amount: Moderate. Pollen color: RHS 22A.

*Pistil.*—Quantity per flower: 1. Length: 0.1 cm. Stigma: Shape: Square. Color: RHS 155C. Style: Length (cm): 0.1 cm. Color: RHS 157A. Ovary color: RHS 155A.

Seed set: Sets seed; achenes are 3 and 4-sided, prominent wings 1.2 cm long, 1.3 cm wide and RHS 166D in color.

Disease and insect resistance: Selected for tolerant to heat; grows well in the midwest with harvest from late April through September.

Market use: Cooking.

COMPARISON WITH PARENTAL AND COMMERCIAL VARIETIES

Table 1 shows the differences between the open-pollinated parent 'Victoria' (unpatented) and 'GARrusarsabzar'.

TABLE 1

Comparison with Parental line

| Characteristic | 'GARrusarsabzar' | Parent 'Victoria' |
|---|---|---|
| Petiole color | RHS 53A | RHS 145C overlaid with RHS 47C to RHS 47D |
| Petiole length | 35.0 cm to 40.0 cm | 25.0 cm to 30.0 cm |
| Petiole width | 1.5 cm | 2.0 cm |

Table 2 shows the differences between 'GARrusarsabzar' and the commercial line 'Crimson Red' (unpatented).

TABLE 2

Comparison with Commercial line

| Characteristic | 'GARrusarsabzar' | 'Crimson Red' |
|---|---|---|
| Petiole color | RHS 53A | RHS 46B |

We claim:

1. A new and distinct variety of rhubarb plant designated 'GARrusarsabzar' as illustrated and described herein.

* * * * *